(12) United States Patent
Ciupik et al.

(10) Patent No.: US 8,900,311 B2
(45) Date of Patent: Dec. 2, 2014

(54) INTERVERTEBRAL SPINAL IMPLANT

(71) Applicant: Lfc Spolka z o.o., Zielona Gora (PL)

(72) Inventors: Lechoslaw Franciszek Ciupik, Zielona Gora (PL); Jacek Cecek, Zielona Gora (PL); Pawel Powchowicz, Zielona Gora (PL); Lukasz Jedrych, Zielona Gora (PL)

(73) Assignee: Lfc Spolka z o.o., Zielona Gora (PL)

( * ) Notice: Subject to any disclaimer, the term of this patent is extended or adjusted under 35 U.S.C. 154(b) by 239 days.

(21) Appl. No.: 13/654,778

(22) Filed: Oct. 18, 2012

(65) Prior Publication Data
US 2013/0096685 A1 Apr. 18, 2013

(30) Foreign Application Priority Data

Oct. 18, 2011 (PL) .......................................... 396686

(51) Int. Cl.
*A61F 2/44* (2006.01)
*A61F 2/46* (2006.01)
*A61F 2/30* (2006.01)

(52) U.S. Cl.
CPC ............ *A61F 2/4465* (2013.01); *A61F 2/4611* (2013.01); *A61F 2002/4475* (2013.01); *A61F 2002/30879* (2013.01); *A61F 2002/30538* (2013.01); *A61F 2002/30772* (2013.01); *A61F 2002/30131* (2013.01); *A61F 2002/30915* (2013.01); *A61F 2002/30912* (2013.01); *A61F 2002/30383* (2013.01); *A61F 2002/30321* (2013.01); *A61F 2002/30909* (2013.01); *A61F 2002/30881* (2013.01); *A61F 2002/30308* (2013.01); *A61F 2002/30822* (2013.01); *A61F 2002/30029* (2013.01); *A61F 2002/30827* (2013.01)
USPC ...................................................... 623/17.16

(58) Field of Classification Search
USPC ........................................................ 623/17.16
See application file for complete search history.

(56) References Cited

U.S. PATENT DOCUMENTS 6,159,245 A 12/2000 Meriwether et al.
2003/0069640 A1 4/2003 Ferreira et al.
(Continued)

FOREIGN PATENT DOCUMENTS

EP 1683593 A2 7/2006
FR 2955025 A1 7/2011
(Continued)

OTHER PUBLICATIONS

International Search Report and Written Opinion of the International Searching Authority re PCT/PL2012/000107; dated Feb. 7, 2013.
(Continued)

*Primary Examiner* — Andrew Yang
*Assistant Examiner* — Olivia C Chang
(74) *Attorney, Agent, or Firm* — Hovey Williams LLP

(57) ABSTRACT

An intervertebral spinal implant includes a shaped body with a first bearing side, a second bearing side located opposite to the first bearing side, a front part, a rear part, a concave side and a convex side. The concave side and the convex side are both connected to the bearing sides as well as to the front part and the rear part. The first bearing side and the second bearing side are each provided with at least two projections for penetration within a vertebral body's wall. The projections are formed by elongated sliding-guiding runners which extend in a diverging manner from the concave side of the body towards the convex side of the body. The sliding-guiding runners extend in a curved manner so that they also extend from the concave side of the body towards the rear part of the body in addition to extending towards the convex side of the body. The sliding-guiding runners are provided with a smooth surface facing the convex side of the body and with a rough surface facing the concave side of the body.

19 Claims, 5 Drawing Sheets

(56) References Cited

U.S. PATENT DOCUMENTS

Figure 1:
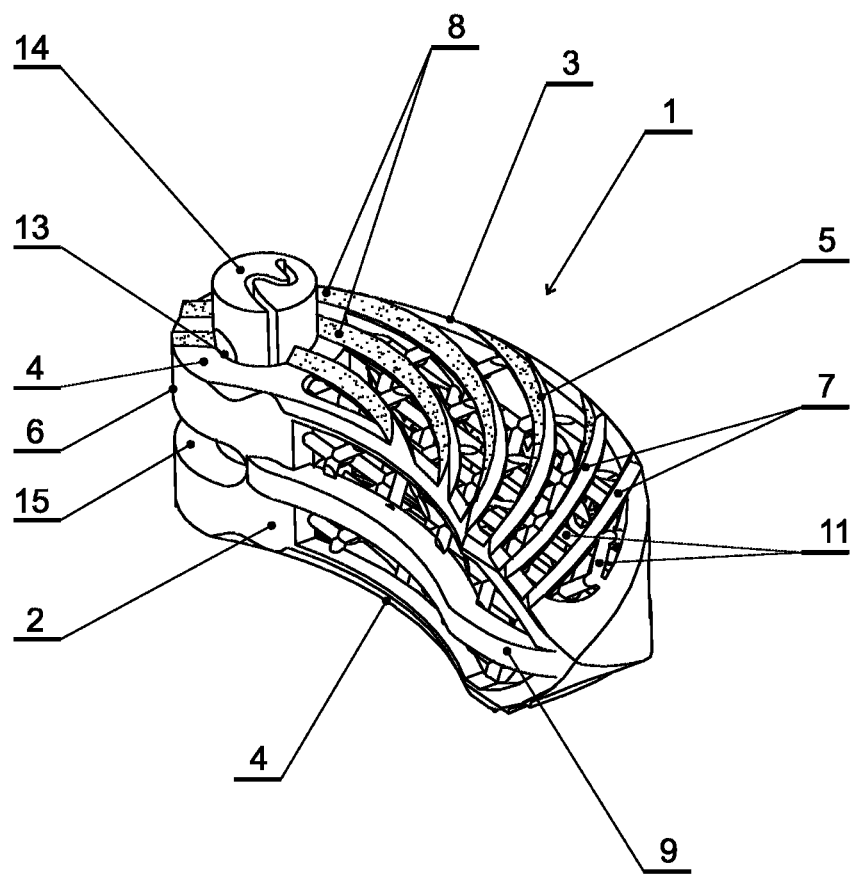

| | | |
|---|---|---|
| 2005/0177238 A1 | 8/2005 | Khandkar |
| 2007/0282441 A1 | 12/2007 | Stream et al. |
| 2008/0021557 A1 | 1/2008 | Trieu |
| 2008/0140085 A1 | 6/2008 | Gately et al. |
| 2009/0157186 A1 | 6/2009 | Magerl |
| 2010/0049325 A1 | 2/2010 | Biedermann et al. |
| 2010/0094422 A1 | 4/2010 | Hansell et al. |
| 2010/0234903 A1 | 9/2010 | Biedermann et al. |
| 2010/0292801 A1 | 11/2010 | Hansell et al. |

FOREIGN PATENT DOCUMENTS

| | | |
|---|---|---|
| WO | WO 2009/025884 A2 | 2/2009 |
| WO | 2010045231 A1 | 4/2010 |

OTHER PUBLICATIONS

International Preliminary Report on Patentability and Written Opinion if the International Searching Authority re PCT/PL2012/000107; dated May 1, 2014.

INTERVERTEBRAL SPINAL IMPLANT

RELATED APPLICATION

The present application claims the benefit of and priority from Polish Patent Application No. P-396686, filed Oct. 18, 2011, the entire disclosure of which is hereby incorporated by reference herein.

BACKGROUND

1. Field

The invention relates to the intervertebral spinal implant, which finds application in surgical spinal treatment in order to maintain proper distance between adjacent vertebrae and stabilization of treated spinal segment.

2. Discussion of Prior Art

From the patent application US 2010/0049325 an intervertebral implant is known, which consists of two parts, which are introduced between two vertebrae. A first part has a first contact surface extending between its two ends a first guide surface extending out from the first contact surface. A second part has a second contact surface extending between its ends, and a second guide surface recessed into the second contact surface. The first guide surface and the second guide surface cooperate so that the first contact surface of the first part can slide relative to the second contact surface of the second part with a translation motion guided by the cooperating structures of the first and second guide surfaces. The height of the intervertebral implant can be altered by shifting the first part and the second part relative to each other by moving the contact surfaces relative to each other by using the cooperating guide surfaces. The inconvenience of this solution is small overall surface of holes allowing for a bony overgrowth, possibility of not intended change of the implant's height as a result of the shifting of two parts relative to each other and a lack of means, which prevent sliding the implant off the intervertebral space.

From the patent application US 2009/0157186 an intervertebral implant is known, which comprises a first part and a second part, which may be uniportally implanted in a disc cavity and connected to each other therein. The parts comprise an opening for housing spongiosa or bone replacement material. Both parts have connector means, which engage with each other on implantation in the disc cavity and thus connect both parts to each other. At least one part preferably comprises a groove in which a spring of the other part may be introduced in a sliding manner. The groove and the spring are arranged on the inner narrow faces of both parts which are to come together. The implant may be implanted uniportally through a transforaminal or an extraforaminal opening. The inconvenience of this solution is a very small bearing surface of the implant, which causes great pressure of the implant on the bone, and penetration of the implant into the bone. Both implant's parts are wide, which requires relatively big surgical approach. The implant doesn't comprise means, which prevent shifting of the implant and sliding the implant off the intervertebral space.

From the patent application WO 2010/045231 intervertebral spacer is known, which comprises implant installed between adjacent vertebral bodies. The implant is provided with support body and a rotatable insert. The support body can be curved or has a shape of an arch extending in lateral direction between proximal and distal frontal part of the implant. Distal frontal part of the implant can have a conical end. Proximal frontal part is provided with a hole, in which is situated element for cooperation with installation tool. In one embodiment the implant is provided with a hole which allows for bony overgrowth through the implant and bony fusion after implantation. Opposite surfaces of the implant are provided with projections or teeth preventing sliding the implant off the intervertebral space. The inconvenience of this solution is very small bearing surface of the implant, which causes great pressure of the implant on the bone, and penetration of the implant into the bone. Because of a location of the overgrowth hole on lateral walls of the implant, it has got limited bony overgrowth.

An intervertebral spinal implant in a form of a body with a concave side, a convex side and bearing sides provided with at least two projections for penetration within vertebral body's wall is disclosed in US 2008/0140085 A1. The projections are formed by elongated edges which extend in a diverging manner from the concave side of the body towards the convex side of the body.

Installation of known implants requires performance of quite great intervertebral distraction, which stems from sharp, protruding anchoring elements in implants, which hamper introduction of the implant into proper place between vertebral bodies. Anchoring of the implant can cause loss of distraction. After installation of the implant into intervertebral space, because of its anchoring, there is no possibility to perform correction of its seating. Small overall surface of overgrowth holes, or their location on the implant in improper places don't provide required spinal stabilization.

SUMMARY

With respect to the mentioned state of the art it is an objective of the present invention to provide an advantageous intervertebral spinal implant.

This objective is achieved by an intervertebral spinal implant as claimed in claim 1. The depending claims contain further developments of the invention.

Free of these inconveniences is intervertebral spinal implant in a form of shaped body, in which convex side and concave side connects with opposite to each other bearing sides provided with projections for penetration (diving in) vertebral body's wall, and having holes for bony tissue and hole, in which is situated an element cooperating with installation tool, and in which, according to the invention, each bearing side is provided with at least two sliding-guiding runners, constituting projections for penetration (diving in) in vertebral body's wall. Sliding-guiding runners are situated divergently from the convex side of the body towards convex side and posterior part of the body. Sliding-guiding runners are provided with a smooth surface from the convex side of the body, and with a rough surface from the concave side of the body. Concave side of the body is provided with at least one guide, and convex side of the body with at least one guideline. The bottom of the guideline constitutes formed by rods spatial (three-dimensional) framework, which fulfills inside of the body and constituting a bearing construct for sliding-guiding runners and the guide, and also facilitating bony overgrowth.

Preferably, sliding-guiding runners are provided with shaped gaps locking self-acting withdrawal of the implant from intervertebral space. Preferably, the guideline is provided with a projection, which limits shifting of the guide of the cooperating implant within.

Preferably on the posterior part of the body, there is located a projection limiting the movement of installation tool with respect to the implant.

Preferably, sliding-guiding runners have got in a cross section shape similar to a triangle or trapezium or rectangular or two arches.

The advantage of the invention is provision of bearing surfaces with sliding-guiding runners allowing for self-guiding and controlled situating of the implant in the most suitable biomechanically place. Self-guiding of the implant allows for use of one implant or two cooperating with each other implants owing to the guide and the guideline on their sides. After introducing one implant into intervertebral space, from the same surgical approach can be introduced the second implant, by locating the guide of the first implant in the guideline of the second implant. Sliding-guiding runners on bearing sides of the implant fulfills, next to the bearing function, anchoring function and also allows for bony overgrowth. Filling the inner of the body with formed by rods spatial (three dimensional) framework increases stiffness of the implant and prevents deformation of runners and implant's sides, and also favors bony overgrowth through the inner of the implant. Equipment of sliding-guiding runners with rough surface favors bony overgrowth and also increases implant's stabilization in intervertebral space.

BRIEF DESCRIPTION OF THE DRAWING FIGURES

Figure 2:
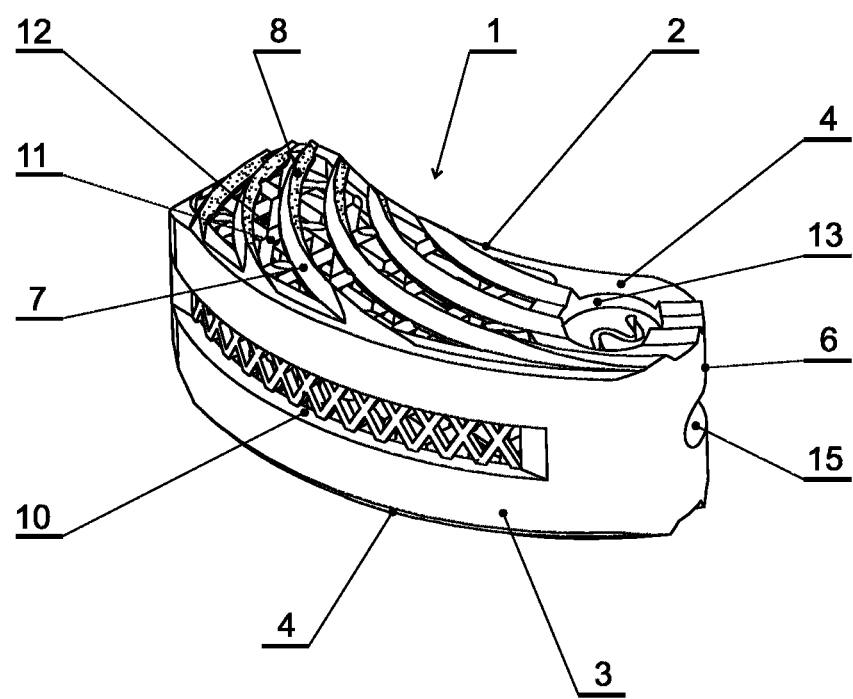
Figure 3:
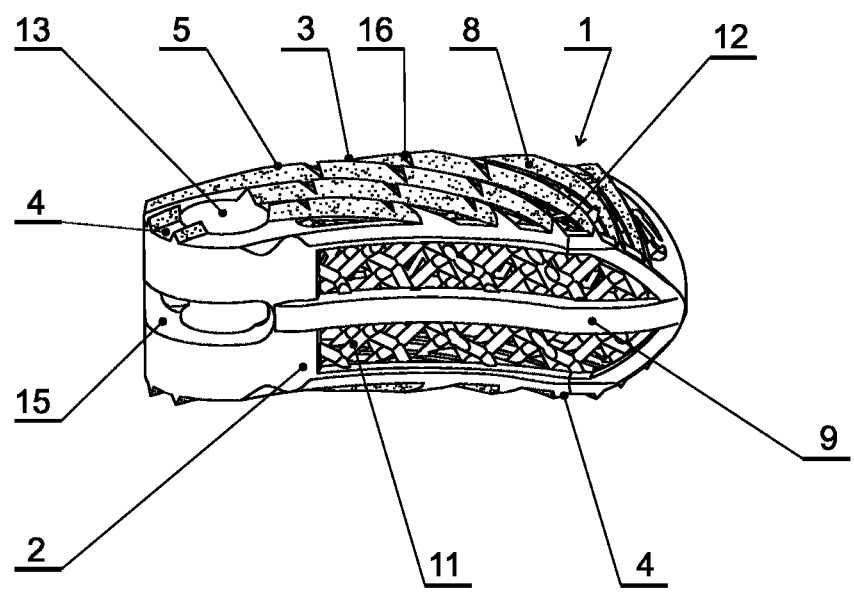
Figure 4:
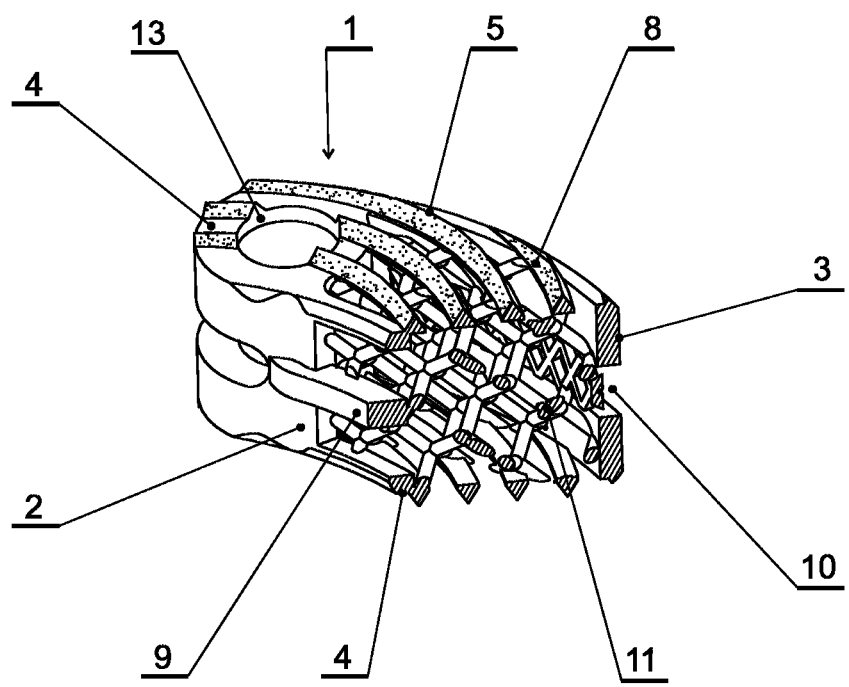
Figure 5:
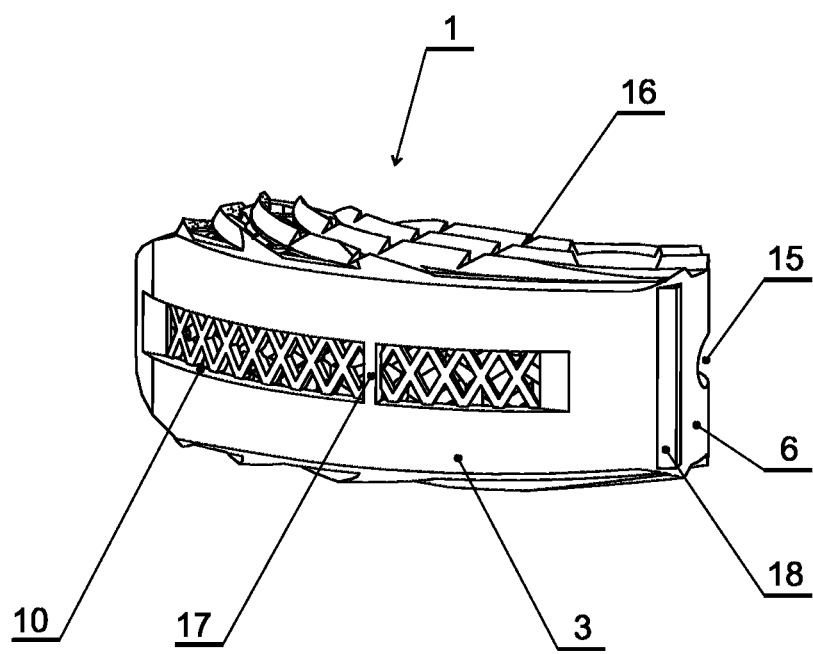

An intervertebral spinal implant according to the invention is introduced in exemplary embodiments described in detail below, wherein:

FIG. 1 illustrates the implant in a frontal view, showing its concave side and bearing side, with partially pulled out of the hole element cooperating with installation tool, FIG. 2 illustrates the implant in a side view showing rear part of the implant and the bearing side, FIG. 3 illustrates in a concave-side view the embodiment of the implant in which sliding-guiding runners are provided with shaped gaps, FIG. 4 illustrates the implant in a cross-section, and FIG. 5 illustrates in a convex-side view the embodiment of the implant with the projection in the guideline and the projection on the surface of the rear part of the body.

The drawing figures do not limit the present invention to the specific embodiments disclosed and described herein. The drawings are not necessarily to scale, emphasis instead being placed upon clearly illustrating the principles of the preferred embodiment.

DETAILED DESCRIPTION OF THE PREFERRED EMBODIMENTS

An intervertebral spinal implant has the form of a shaped body 1, in which concave side 2 and convex side 3 connect with opposite bearing sides 4. Each bearing side 4 of the body 1 is provided with at least two, constituting projections for penetration within vertebral body's wall, sliding-guiding runners 5 situated divergently from the concave side 2 of the body 1 towards convex side 3 and posterior part 6 of the body 1. Sliding-guiding runners 5 are provided with a smooth surface 7 from the convex side 3 of the body 1, and with a rough surface 8 from the concave side 2 of the body 1.

Concave side 2 of the body 1 is provided with a guide 9, and convex side 3 of the body 1 with a guideline 10. The bottom of the guideline 10 constitutes formed by rods spatial (three-dimensional) framework 11, which fulfills inside of the body 1 and constitutes a bearing construct for sliding-guiding runners 5 and the guide 9.

Sides of the body 1 between sliding-guiding runners 5 constitute overgrowing holes 12 allowing for bony overgrowth to the inside of the body 1 fulfilled with the spatial framework 11.

In the rear part 6 the body 1 is provided with a hole 13, in which is situated element 14 cooperating with installation tool. The installation tool is introduced through the installation hole 15.

In embodiments presented on FIG. 3 and FIG. 5 sliding-guiding runners 5 are provided with shaped gaps 16 increasing effectiveness of fixation of the implant in vertebral body.

In the embodiment of the implant illustrated on FIG. 5, the guideline is provided with a projection 17 limiting shifting of the second implant's guide 9, sliding within the guideline 10 of the first implant.

In the embodiment of the implant illustrated on FIG. 5 on the surface of the rear part 6 of the body 1 is situated the projection 18 limiting movement of installation tool with respect to the implant.

Sliding-guiding runners 5 have in a cross-section shape similar to the triangle. There is a possibility to perform these runners 5 in another shape of cross-section, like trapezium, rectangular or a shape of two arches.

Features of the disclosed embodiments can be represented by the following clauses:

1. An intervertebral spinal implant in the form of a shaped body, in which concave side and convex side connect with opposite to each other bearing sides providing with projections for penetration within vertebral body's wall and having holes for bony tissue and a hole, in which is situated element for cooperation with installation tool, where: each bearing side 4 of the body 1 is provided with at least two, constituting projections for penetration within vertebral body's wall, sliding-guiding runners 5 situated divergently from the concave side 2 of the body 1 towards convex side 3 and rear part 6 of the body 1 and provided with a smooth surface 7 from the convex side 3 of the body 1, and with a rough surface 8 from the concave side 2 of the body 1, the concave side 2 of the body 1 is provided with at least one guide 9, and convex side 3 of the body 1 with at least one guideline 10 bottom of which constitutes formed by rods spatial (three-dimensional) framework 11, which fulfills inside of the body 1 and constitutes a bearing construct for sliding-guiding runners 5 and the guide 9.

2. Intervertebral spinal implant according to the clause 1, where sliding-guiding runners 5 are provided with shaped gaps 16.

3. Intervertebral spinal implant according to the clause 1, where the guideline 10 is provided with the projection 17 limiting shift within of the guide 9 of cooperating implant.

4. Intervertebral spinal implant according to the clause 1, where on the surface of the rear part 6 of the body 1 is situated the projection 18 limiting the movement of the installation tool according to the implant.

5. Intervertebral spinal implant according to the clause 1, where sliding-guiding runners 5 have in a cross-section shape similar to the triangle.

The preferred forms of the invention described above are to be used as illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

What is claimed is:

1. An intervertebral spinal implant comprising:
a shaped body with a first bearing side, a second bearing side located opposite to the first bearing side, a front part, a rear part, a concave side and a convex side,
said concave side and said convex side both being connected to the bearing sides as well as to the front part and the rear part,
said first bearing side and said second bearing side each being provided with at least two projections for penetration within a vertebral body's wall, holes for bony tissue and a hole, in which an element for cooperation with an installation tool is situated, where the projections are formed by elongated sliding-guiding runners which extend in a diverging manner from the concave side of the body towards the convex side of the body,
said sliding-guiding runners extend in a curved manner so that they also extend from the concave side of the body towards the rear part of the body in addition to extending towards the convex side of the body,
said sliding-guiding runners being provided with a smooth surface facing the convex side of the body and with a rough surface facing the concave side of the body.

2. The intervertebral spinal implant according to claim 1, said sliding-guiding runners being provided with shaped gaps.

3. The intervertebral spinal implant according to claim 2, said sliding-guiding runners having a triangular cross-section, a trapezoidal cross-section, a rectangular cross-section, or a cross-section in the shape of a pointed arch.

4. The intervertebral spinal implant according to claim 3, said concave side of the body being provided with at least one guide,
said convex side of the body being provided with at least one guideline which can cooperate with a guideline of a neighboring intervertebral spinal implant.

5. The intervertebral spinal implant according to the claim 4,
said bottom of the guideline being formed by a mesh.

6. The intervertebral spinal implant according to the claim 5,
said guideline being provided with a projection limiting a movement of a guide of a cooperating intervertebral spinal implant.

7. The intervertebral spinal implant according to claim 6, said shaped body including a projection limiting the movement of an installation tool, with the projection being present on the surface of the rear part of the body.

8. The intervertebral spinal implant according to claim 7, said inside of the body being formed by a spatial framework which constitutes a bearing construct for the sliding-guiding runners and, if present, for the guide.

9. The intervertebral spinal implant according to claim 4, said inside of the body being formed by a spatial framework which constitutes a bearing construct for the sliding-guiding runners and, if present, for the guide.

10. The intervertebral spinal implant according to claim 1, said sliding-guiding runners having a triangular cross-section, a trapezoidal cross-section, a rectangular cross-section, or a cross-section in the shape of a pointed arch.

11. The intervertebral spinal implant according to claim 1, said concave side of the body being provided with at least one guide,
said convex side of the body being provided with at least one guideline which can cooperate with a guideline of a neighboring intervertebral spinal implant.

12. The intervertebral spinal implant according to the claim 11,
said guideline being provided with a projection limiting a movement of a guide of a cooperating intervertebral spinal implant.

13. The intervertebral spinal implant according to the claim 11,
said bottom of the guideline being formed by a mesh.

14. The intervertebral spinal implant according to the claim 13,
said guideline being provided with a projection limiting a movement of a guide of a cooperating intervertebral spinal implant.

15. The intervertebral spinal implant according to claim 11, said shaped body including a projection limiting the movement of an installation tool, with the projection being present on the surface of the rear part of the body.

16. The intervertebral spinal implant according to claim 11, said inside of the body being formed by a spatial framework which constitutes a bearing construct for the sliding-guiding runners and, if present, for the guide.

17. The intervertebral spinal implant according to claim 1; said shaped body including a projection limiting the movement of an installation tool, with the projection being present on the surface of the rear part of the body.

18. The intervertebral spinal implant according to claim 2, said inside of the body being formed by a spatial framework which constitutes a bearing construct for the sliding-guiding runners and, if present, for the guide.

19. The intervertebral spinal implant according to claim 1, said inside of the body being formed by a spatial framework which constitutes a bearing construct for the sliding-guiding runners and, if present, for the guide.

* * * * *